United States Patent
Makovec et al.

(10) Patent No.: US 7,294,648 B2
(45) Date of Patent: Nov. 13, 2007

(54) ANTHRANYL DERIVATIVES HAVING AN ANTICHOLECYSTOKININ ACTIVITY (ANTI-CCK-1), A PROCESS FOR THEIR PREPARATION, AND PHARMACEUTICAL USE THEREOF

(75) Inventors: Francesco Makovec, Lesmo (IT); Antonio Varnavas, Trieste (IT); Lucia Lassiani, Trieste (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 447 days.

(21) Appl. No.: 10/523,075

(22) PCT Filed: Jul. 23, 2003

(86) PCT No.: PCT/IB03/02922

§ 371 (c)(1),
(2), (4) Date: Jan. 25, 2005

(87) PCT Pub. No.: WO2004/013087

PCT Pub. Date: Feb. 12, 2004

(65) Prior Publication Data
US 2006/0111304 A1    May 25, 2006

(30) Foreign Application Priority Data
Jul. 26, 2002    (IT) ................ TO2002A0674

(51) Int. Cl.
*A61K 31/404* (2006.01)
*C07D 209/04* (2006.01)
(52) U.S. Cl. .............. 514/419; 548/469; 548/490; 548/491; 514/415
(58) Field of Classification Search ............ 548/469, 548/490, 491; 514/415, 419
See application file for complete search history.

(56) References Cited

OTHER PUBLICATIONS

Antonio Varnavas, et al.: "Anthranilic acid derivatives: a new class of non-peptide CCKI receptor antagonists" Bioorganic & Medicinal Chemistry, vol. 11, No. 5, Mar. 6, 2003, pp. 741-751, XP002265140.
Antonio Varnavas et la.: "Synthesis of N-terminal substituted anthranilic acid dimer derivatives for evaluation on CCK receptors", FARMACO, vol. 56, No. 8, Aug. 1, 2001.
Antonio Varnavas, et al.: "Synthesis of new antrhanilic acid dimmer derivatives and their evaluation on CCK receptors", vol. 55, No. 5, 2000, pp. 369-375 XP002265142.

*Primary Examiner*—Golam M. M. Shameem
(74) *Attorney, Agent, or Firm*—Sughrue Mion Pllc.

(57) ABSTRACT

Anthranylic compounds having anti-CCK activity of general formula (I) in which, n is a whole number lying between 0 and 7; $R_1$ is chosen independently from the groups (II), in which $X_1$ is chosen independently from, S, O, $NR_2$ and $X_2$ is a group chosen from: H, $C_1$-$C_4$ alkyl, F, Cl, $CF_3$, $OCH_3$, $OC_2H_5$, CN; $R_2$ is chosen from H or $CH_3$; $R_3$ is chosen from H, $CH_3$, F, Cl, $CF_3$, $OCH_3$; $R_4$ is chosen from the groups: H, —S—$(CH_2)$m-$R_5$, —$SO_2$—$(CH_2)$m-$R_5$ (n different from 0), a branched alkyl group, a cyclo alkyl, a cyclo alkenyl, the group 1 or 2 adamantile, a phenyl group optionally substituted; $R_5$ is chosen from the groups: H, linear or branched alkyl, cyclo alkyl, the group 1 or 2 adamantile, a suitably substituted phenyl group (I)

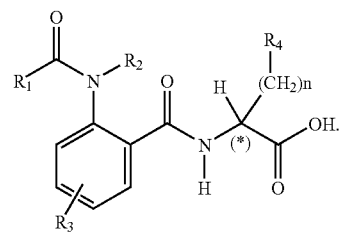

8 Claims, No Drawings

ANTHRANYL DERIVATIVES HAVING AN ANTICHOLECYSTOKININ ACTIVITY (ANTI-CCK-1), A PROCESS FOR THEIR PREPARATION, AND PHARMACEUTICAL USE THEREOF

This is a National Stage entry of Application No. PCT/IB2003/002922 with an international filing date of Jul. 23, 2003, which was published under PCT Article 21(2) as WO 2004/013087, the complete disclosures of which is incorporated into this application by reference.

The subject of the present invention is new derivatives of anthranylic acid which can be represented by the following general formula (I) and in which:

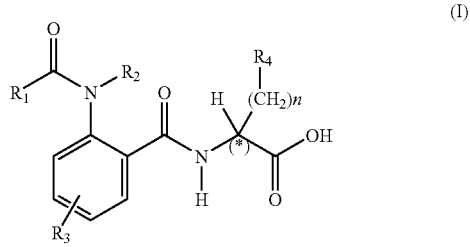

n is a whole number lying between 0 and 7;
$R_1$ is chosen independently from the groups:

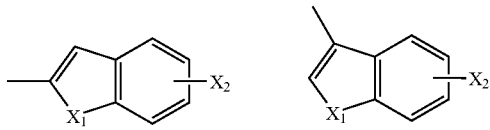

in which $X_1$ is chosen independently from S, O, $NR_2$ and $X_2$ is a group chosen independently from: H, $C_1$-$C_4$ linear or branched alkyl F, Cl, $CF_3$, $OCH_3$, $OC_2H_5$, CN;

$R_2$ is chosen independently from H or $CH_3$;

$R_3$ is chosen independently from H, $CH_3$, F, Cl, $CF_3$, $OCH_3$;

$R_4$ is chosen independently from the groups: H, —S—$(CH_2)$m-$R_5$, —$SO_2$—$(CH_2)$m-$R_5$ (n different from 0) in which m is a whole number lying between 0 and 2, a branched alkyl group formed by 3 to 6 carbon atoms, a cycloalkyl formed by 3 to 10 carbon atoms, a cycloalkenyl formed by 4 to 6 carbon atoms, the group 1 or 2-adamantyl, a simple, mono- or bi-substituted phenyl group, in which the substituents can be chosen independently from halogens, a linear alkyl group formed by 1 to 3 carbon atoms, a branched alkyl group formed by 3 to 6 carbon atoms, an alkoxylic group formed by 1 to 3 carbon atoms, —$NO_2$, —$CF_3$, —CN;

$R_5$ is chosen from groups: H, a linear alkyl group formed by 1 to 3 carbon atoms, a branched alkyl group formed by 3 to 6 carbon atoms, a cycloalkyl formed by 3 up to 10 carbon atoms, a group 1 or 2-adamantyl, a simple, mono- or bi-substituted phenyl group in which the substituents can be chosen independently from other halogens, a linear alkyl group formed by 1 to 3 carbon atoms, a branched alkyl group formed by 3 to 6 carbon atoms, an alkoxylic group formed by 1 to 3 carbon atoms, —$NO_2$, —$CF_3$, —CN.

The stereochemistry of the chiral centre, indicated with an asterix (*) in the formula (I) can be R(Rectus), racemic [R(Rectus), S (Sinister)] or S (Sinister).

Preferably, n is between 1 and 2; $R_1$ is preferably chosen between the groups 2-indolyl, 2-indolyl substituted independently with the flouro group in position 5 or with the methyl group in position 1; $R_3$ is preferably chosen from the groups H, $CH_3$, F, Cl; $R_4$ is preferably chosen from the phenyl group or mono substituted with the methyl groups, methoxy and $CF_3$ groups, whilst the stereochemistry of the compound claimed on the chiral centre indicated with an asterix in the formula (I) is preferably in the racemic form (R, S) or R(Rectus).

Further preferred sub classes are defined in the following claims and their combinations.

The compounds of the present invention are shown to be potent antagonists for the receptors CCK-1(CCK-A) of cholecystokinin (CCK). It is therefore thought that they can be used with advantage in the therapy of various pathologies of man tied to lack of balance of CCK or other related bioactive polypeptides, and to their peripheral levels in the gastrointestinal tract, and at the level of the central nervous system (CNS) or other organs and systems in which such bioactive peptides perform a physiological or pathological role. Thus, for example, one can recognise in advance an advantageous use of these compounds for the treatment, at the gastrointestinal level, of pathologies relating to the motility of organs such as gall bladder, stomach and intestine. In particular, in the case of biliary colic (cirrhosis) by cholecystitis, in the gastro-esophical reflux (GERD) due to an anomalous functioning of the lower esophical sphincter (LES) as well as in irritable bowel syndrome (IBS). Other pathologies of the digestive apparatus in which the subject compounds can be used with advantage, strictly related to the secretagogue function and to the trophic function that CCK performs through the CCK-1 receptors in organs which are the cradle of the gastro intestinal apparatus, are acute and chronic pancreatitis as well as various tumours in which CCK and other bioactive peptides related to it act as growth factors. Alongside the pathologies which involve the gastro intestinal apparatus are multiple actions which involve CNS and in which the CCK-producing system seems to perform an important role. Anorexia, anxiety, panic, depression, schizophrenia, distress associated with tumours etc, are some of the physio pathological situations of wide social impact in which it is considered that a compound on the subject of the invention can be used with advantage.

Until now, receptor antagonists of CCK-1 have been assigned to numerous chemical classes. Among these are indicated benzodiazepam derivatives such as, for example devozopide (L-364,718) (Mol. Pharmacol. 30 (212), 1986) and FK480 (J. Pharmacol. Exp. Ther. 268 (571) (1994), numbing derivates such for example SR 27897 (Eur. J. Pharmacol. 232 (13), 1993) and T-0632 (Eur. J. Pharmacol. 304 (147), 1996) derivatives of glutamic acid such as lorglumide and loxyglumide (gastrin and cholecystokinin, Bali and Martinez (Eds.), Elsevier (45), 1987), derivatives of aspartic acid such as 2-NAP (Br. J. Pharmacol. 108 (734), 1993), quinazolinone having mixed CCK-1 and CCK-2 antagonist activity [U.S. Pat. No. 5,756,502 (1998)].

All these studies demonstrate that there is a strong therapeutic demand to find new pharmaceuticals having anti-CCK-1 activity which are potent, selective and well tolerated. Recently derivatives of anthranilic acid have been described [TO 95-000554 (1995)] which however are antagonist products of the receptor subtype 2 (B) of CCK, whilst anti CCK-1 derivatives of anthranilic acid were not known until now.

Pharmaceutical forms of the compounds forming the subject of the invention can be prepared according to conventional techniques such as, for example, as tablets, capsules, suspensions, solutions and suppositories, patches or as solid preparations for oral use having modified release and can be administered orally, parenterally, nasally, rectally and transdermally.

The active ingredients are administered to the patient typically in the region of 0.1 to 10 mg/kg of bodyweight per dose. For parenteral administration it is preferable to use a hydrosoluble salt of the subject compound as the sodium salt or another non toxic and pharmaceutically acceptable salt. Substances commonly utilised in the pharmaceutical field as excipients such as diluents, binders, aromatisers, separating agents, colourants, humectants, sweeteners, natural or synthetic polymers etc. can be used as inactive ingredients.

The method used for the preparation of compounds forming the subject of the invention comprises the following steps:

a) Reacting in stoichiometric ratio the chloride of the methyl ester of suitable amino acids of formula (V) in which n and $R_4$ have the previously indicated significance and have the chiral centre in the desired configuration with the isatoic an hydride of the formula (IV) suitably substituted with $R_2$ and $R_3$ in which $R_2$ and $R_3$ have the above indicated significance, in the presence of a tertiary amine such as, for example, triethylamine, in an inert solvent and at a temperature lying between +10° and the boiling temperature of the solvent, to give the N-anthranyl-amino acid ethyl esters of formula (III) (see diagram 1, phase I).

b) Reacting the anthranilic derivatives of formula (III), in which n, $R_2$, $R_3$ and $R_4$ have the above indicated significance, with an equivalent quantity of acyl chloride of formula $R_1$—COCl, in which $R_1$ has the above indicated significance, preferably in pyridine and at a temperature lying between 0° and +30° and recovering from the reaction mixture the acyl-derivatives of formula (II) (see diagram 1, phase II).

c) Hydrolysing the esters of formula (II), in which n, $R_1$, $R_2$, $R_3$ and $R_4$ have the above indicated significance, in an inner solvent (such as, for example, tetrahydrofuran), with an aqueous solution of a strong inorganic base (such as lithium hydroxide), for a time period lying between 4 and 48 hours. After evaporation of the solvent, acidification and recovery of the reaction mass and with the conventional methods the derivatives of the anthranylic acid of formula (I) in which n, $R_1$, $R_2$, $R_3$ and $R_4$ have the above indicated significance and with the chiral centre in the desired configuration (see diagram 1, phase III).

The ethyl esters of the starting amino acids of formula (V), the amino acids from which they derive as well as the suitably substituted isatoic an hydrides of formula (IV) are commercially available and have been prepared with conventional methods described in the literature.

The acyl chlorides of formula $R_1$—COCl, in which $R_1$ has the previously indicated significance, have been prepared according to conventional methods, (preferably using phosphorous pentachloride) in an inert solvent at a temperature lying between −10° and +20°.

The series of operations of the process according to the above invention are illustrated overall in the following (diagram 1):

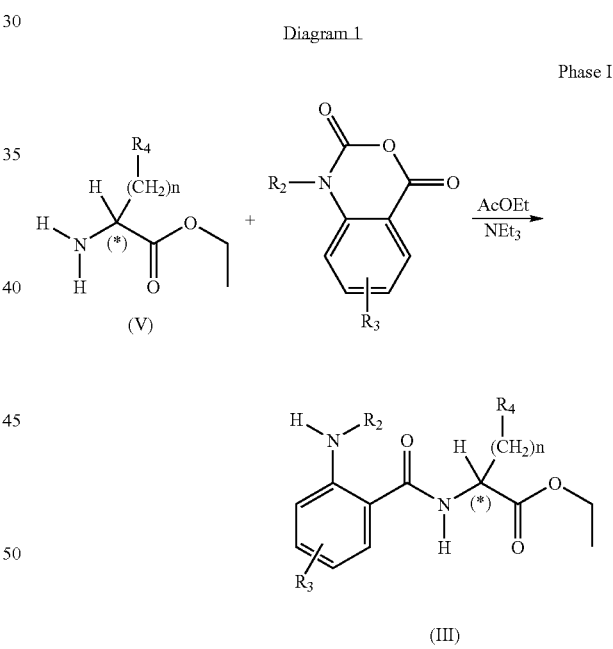

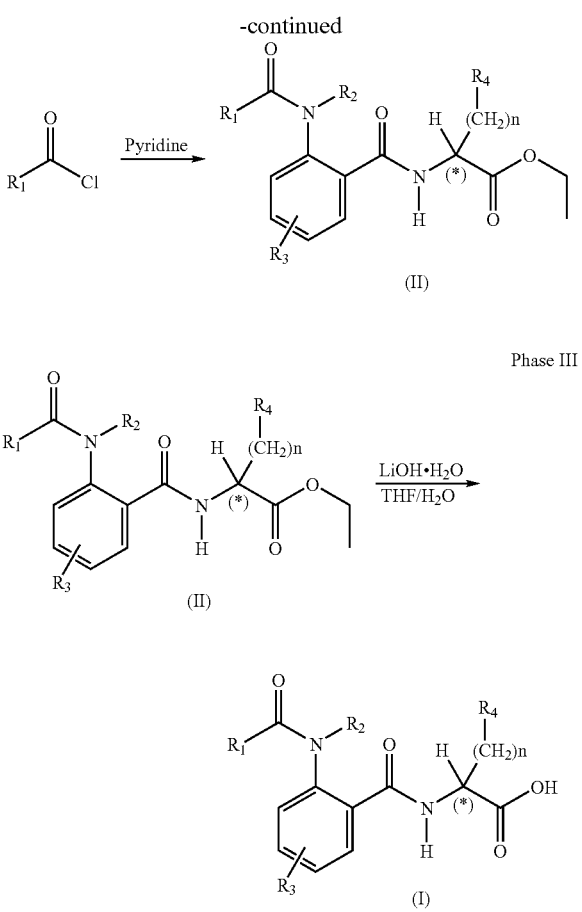

The following examples are given better to illustrate the invention.

EXAMPLE 1

Preparation of: ethyl ester of 2(R,S)-(2-amino benzoylamine)-3-phenyl propionic acid (General Formula III)

To 22.9 g (0.1 moles) of the hydrochlorate of DL-phenylalanine ethyl ester, suspended in 500 ml of ethyl acetate, were added 13.9 ml of triethylamine (0.1 moles) and, under agitation, 16.3 g (0.1 moles) of isatoic anhydride. After heating to reflux for 4 hours the reaction mixture was cooled to ambient temperature and filtered. The filter was washed with NaOH 1N and then with water. The organic phase was dehydrated and evaporated and the oily residue rendered friable by 40-600 petroleum ether. The raw product is crystallised by ethyl acetate/hexane 1:1 (v/v). After cooling the white solid formed is filtered and dried at 60°, obtaining 25.0 g (0.08 moles) of product with yield of 80% ($C_{18}H_{20}N_2O_3$)

F.p. 85° C. TLC (AcOEt/Hexane 1:1)—Rf: 0.63. $^1$H-NMR (CDCl$_3$): δ 1.24 (t, 3H, —CH$_3$); 3.21 (m, 2H, —CH$_2$—CH<); 4.18 (q, 2H, —CH$_2$—O—); 4.97 (m, 1H, >CH—); 5.45 (s, 2H, —NH$_2$); 6.52 (d, 1H, —NH—); 6.61-7.28 (m, 9H, aromatics).

All the compounds of formula III are synthesised when using the same procedure (see diagram 1-phase I).

EXAMPLE 2

Preparation of: ethyl ester of 2 (R,S)-{2-[(1H-indol-2-carbonyl) amino]-benzoyl-amino}-3-phyemyl-propionic acid (General Formula II)

To a suspension of 16.1 g (0.1 moles) of the indol-2-carboxylic acid in 250 ml of dichloromethane at 0° C. was added in small portions and under agitation 31.2 g (0.15 moles) of phosphorous pentachloride. This was left to react at ambient temperature for 3 hours, dichloromethane was added and the solvent evaporated under vacuum. The chloride of the acid thus formed, dissolved in 50 ml of dichloromethane, was added under agitation to a solution of 31.2 g (0.1 moles) of the ethyl ester of 2 (R,S)-(2-amino-benzoylamino)-3-phenyl-propionic acid in 100 ml of pyridine at a temperature of 0° C. At the end of the addition the reaction mass was held at 0° C. for a further hour and then at ambient temperature for about 12 hours. 250 ml of dichloromethane was added and the organic phase washed with 400 ml of HCl 1N and then with NaOH 0.1N and finally with the saturated solution of NaCl. After drying, the solvent was evaporated and the raw product purified by treatment with hot methanol. After cooling the solid was filtered and dried at 60° C. in an oven, obtaining 35.5 g (0.078 moles) of product with a yield of 78% ($C_{27}H_{25}N_3O_4$)

F.p. 210-211° C. TLC (AcOEt/Hexane 1:1)—Rf: 0.69. $^1$H-NMR (DMSO-d$_6$): δ 1.17 (t, 3H, —CH$_3$); 3.20 (m, 2H, —CH$_2$—CH<); 4.11 (q, 2H, —CH$_2$—O—); 4.79 (m, 1H, —CH<); 6.98 (s, 1H, indol); 7.06-7.82 (m, 12H, aromatics); 8.64 (d, 1H, aromatic); 9.30 (d, 1H, —NH—CH<); 11.95 (s, 1H, —NH— indol); 12.15 (s, 1H, —NH—).

All the compounds of Formula (II) were synthesised using the same procedure (see Diagram 1-Phase II).

EXAMPLE 3

Preparation of: 2 (R,S)-{2-[(1H-indol-2-carbonil) amino]-benzoilamino}-3-phnyl-propionic acid. [compound 1 (General Formula I)-Table 1]

To a suspension of 45.5 g (0.1 moles) of the ethyl ester of 2 (R,S)-{2-[(1H-indol-2-carbonyl) amino]-benzoylamino}-3-phenyl-propionic acid in 1 litre of an H$_2$O/THF 1:1 mixture were added 4.6 g (0.11 moles) of hydrated lithium hydroxide and left under agitation under ambient temperature for 24 hours. The process continues with the evaporation of the organic solvent and the products obtained by precipitation at 0° C. followed by acidification with dilute HCl. The raw product is crystalised by methanol, obtaining 36.3 g (0.085 moles) with yield of 855% ($C_{25}H_{21}N_3O_4$).

F.p. 268-269° C. TLC (AcOEt/MeOH 2:1)—Rf: 0.61. $^1$H-NMR (DMSO-d$_6$): δ 3.27 (m, 2H, —CH$_2$—CH<); 4.79 (m, 1H, >CH—); 6.97 (s, 1H, H indol); 7.06-7.87 (m, 12H, aromatics); 8.64 (d, 1H, H aromatic); 9.21 (d, 1H, —NH—); 11.93 (s, 1H, —NH— indol); 12.28 (s, 1H, —NH—).

EXAMPLE 4

Preparation of: 2 (R)-{2-[(1H-indol-2-carbonyl) amino]-benzoylamino}-3-phenyl-propionic acid: [compound 2 (General Formula I)-Table 1].

The procedure was as described in Examples 1, 2 and 3, starting from chloride of D-phenyl alamine ethyl ester.

Yield: 43%. Formula: $C_{25}H_{21}N_3O_4$ F.p. 271-272° C.; TLC (AcOEt/MeOH 2:1)—Rf: 0.61 Rotatory power: $[\alpha]_D^{25}=+13.6$ (c=0.59, DMF). Optical purity: e.e [HPLC chiral]=98.7%.

Chiral HPLC analytic conditions: CSP-TE-SP-100 column of 250 mm; internal diamteter 4 mm; Detector; UV at 254 nm; Eluent; MeOH/H$_2$O 85/15 (v/v)+20 mM NH$_4$OAc; Flow; 1.00 ml/min; Temperature: 23° C.; Retention time: 5.6 min. against 4.0 min. of the S enantiomer.

EXAMPLE 5

Preparation of: 2(S)-{2-[(1H-indol-2-carbonyl)amino]-benzoylamino}-3-phenyl-propionic acid. [Compound 3 (General Formula I)-Table 1].

Proceed as described in Example 4, starting from hydrochloride of L-phenyl alanine ethyl ester.

Yield: 50%; Formula: $C_{25}H_{21}N_3O_4$. F.p. 270-271° C.; TLC (AcOEt/MeOH 2:1)—Rf: 0.61 Rotatory Power: $[\alpha]_D^{25}=-15.8$ (c=0.57, DMF); Optical purity: e.e [HPLC chiral]>99.5%.

Chiral HPLC analetic conditions: CSP-TE-SP-100, of 250 mm; internal diamter 4 mm; Detector: UV at 254 mm; Eluent MeOH/H$_2$O: 85/15 (v/v)+20 mM NH$_4$OAc; Flow: 1.00 ml/min; Temperature: 23° C.; Retention time: 4.0 min against 5.6 min of the R enantiomer.

All the compounds of formula (I) were synthesised by using the same procedure (see diagram 1). In the following Table 1 are reported some of the compounds thus obtained with some chemical-physical characteristics identified and the solvent of crystallisation, without by this omitting in any way the spirit and scope of the invention itself.

TABLE 1

COMPOUNDS OF GENERAL FORMULA (I)

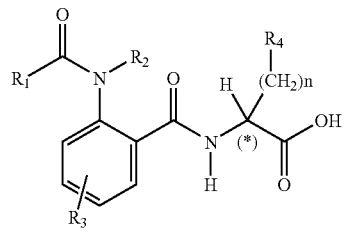

(I)

| COMPOUND | R1 | R2 | R3 | STEREO (Note 1) | n | R4 | SOLVENT OF CRYATALLISATION | FORMULA | FUSION POINT (C) ° | TLC (Rf) (Note 2) |
|---|---|---|---|---|---|---|---|---|---|---|
| 1 | 2-Indolyl | H | H | R, S | 1 | Phenyl | MeOH | C$_{25}$H$_{21}$N$_3$O$_4$ | 268-269 | 0.61* |
| 2 | 2-Indolyl | H | H | R | 1 | Phenyl | MeOH | C$_{25}$H$_{21}$N$_3$O$_4$ | 271-272 | 0.61* |
| 3 | 2-Indolyl | H | H | S | 1 | Phenyl | MeOH | C$_{25}$H$_{21}$N$_3$O$_4$ | 270-271 | 0.61* |
| 4 | 2-Indolyl | H | 5-chloro | R, S | 1 | Phenyl | EtOH 99% | C$_{25}$H$_{20}$ClN$_3$O$_4$ | 268-269 | 0.59* |
| 5 | 1-Methyl-2-indolyl | H | H | R, S | 1 | Phenyl | EtOH 75% | C$_{26}$H$_{23}$N$_3$O$_4$ | 186-188 | 0.50* |
| 6 | 5-Fluoro-2-indolyl | H | H | R, S | 1 | Phenyl | EtOH 99% | C$_{25}$H$_{20}$FN$_3$O$_4$ | 284-286 | 0.42* |
| 7 | 6-Fluoro-2-indolyl | H | H | R, S | 1 | Phenyl | EtOH 99% | C$_{25}$H$_{20}$FN$_3$O$_4$ | 280 dec | 0.66* |
| 8 | 7-Fluoro-2-indolyl | H | H | R, S | 1 | Phenyl | EtOH 99% | C$_{25}$H$_{20}$FN$_3$O$_4$ | 265 dec | 0.66* |
| 9 | 2-Benzofuryl | H | H | R, S | 1 | Phenyl | MeOH | C$_{25}$H$_{20}$N$_2$O$_5$ | 256-257 | 0.25** |
| 10 | 2-Benzothienyl | H | H | R, S | 1 | Phenyl | MeOH | C$_{25}$H$_{20}$N$_2$O$_4$S | 207-209 | 0.33** |
| 11 | 2-Indolyl | H | H | R, S | 1 | 2-Methyl-phenyl | MeOH | C$_{26}$H$_{23}$N$_3$O$_4$ | 278-279 | 0.46* |
| 12 | 2-Indolyl | H | H | R, S | 1 | 4-Methyl-phenyl | MeOH | C$_{26}$H$_{23}$N$_3$O$_4$ | 273-274 | 0.40* |
| 13 | 2-Indolyl | H | H | R, S | 1 | 2-Chloro-phenyl | MeOH | C$_{25}$H$_{20}$ClN$_3$O$_4$ | 281-282 | 0.58* |
| 14 | 2-Indolyl | H | H | R, S | 1 | 3-Chloro-phenyl | MeOH | C$_{25}$H$_{20}$ClN$_3$O$_4$ | 248-249 | 0.52* |
| 15 | 2-Indolyl | H | H | R, S | 1 | 2,6-dichloro-phenyl | MeOH | C25H19C12N3O4 | 287-288 | 0.53* |
| 16 | 2-Indolyl | H | H | R, S | 1 | 3-Methoxy-phenyl | MeOH | C26H23N3O5 | 239-240 | 0.48* |
| 17 | 2-Indolyl | H | H | R, S | 1 | 2-Nitro-phenyl | MeOH | C25H20N4O6 | 253-254 | 0.41* |
| 18 | 2-Indolyl | H | H | R, S | 1 | 4-Nitro-phenyl | MeOH | C25H20N4O6 | 243-244 | 0.49* |
| 19 | 2-Indolyl | H | H | R, S | 1 | 4-Fluoro-phenyl | MeOH | C25H20FN3O4 | 263-264 | 0.54* |
| 20 | 2-Indolyl | H | H | R, S | 2 | Phenyl | MeOH | C26H23N3O4 | 259-260 | 0.48* |
| 21 | 2-Indolyl | H | H | Ra | 2 | Phenyl | AcOEt | C26H23N3O4 | 267-268 | 0.48* |
| 22 | 2-Indolyl | H | H | Sb | 2 | Phenyl | AcOEt | C26H23N3O4 | 267-268 | 0.48* |
| 23 | 5-Fluoro-2-indolyl | H | H | R, S | 2 | Phenyl | EtOH 99% | C26H22FN3O4 | 272-274 | 0.70* |
| 24 | 2-Indolyl | H | H | R, S | 3 | Phenyl | MeOH | C27H25N3O4 | 256-257 | 0.54* |
| 25 | 2-Indolyl | H | H | R, S | 2 | 2-Methyl-phenyl | EtOH 99% | C27H25N3O4 | 257-258 | 0.51* |
| 26 | 5-Fluoro-2-indolyl | H | H | R, S | 2 | 2-Methyl-phenyl | EtOH 96% | C27H24FN3O4 | 262-263 | 0.71* |
| 27 | 1-Methyl-2-Indolyl | H | H | R, S | 2 | 2-Methyl-phenyl | EtOH 75% | C28H27FN3O4 | 158-160 | 0.65* |
| 28 | 2-Indolyl | H | H | R, S | 2 | 2-Nitro-phenyl | EtOH 99% | C26H22N4O6 | 263-264 | 0.44* |
| 29 | 2-Indolyl | H | H | R, S | 2 | 4-Nitro-phenyl | EtOH 99% | C26H22N4O6 | 265 dec | 0.43* |
| 30 | 2-Indolyl | H | H | R, S | 2 | 2-Methoxy-phenyl | EtOH 99% | C27H25N3O5 | 238-239 | 0.67* |
| 31 | 2-Indolyl | H | H | R, S | 2 | 3-Methoxy-phenyl | EtOH 99% | C27H25N3O5 | 233-235 | 0.61* |
| 32 | 5-Fluoro-2-indolyl | H | H | R, S | 2 | 2-Methoxy-phenyl | EtOH 96% | C27H24FN3O5 | 252 dec | 0.73* |
| 33 | 2-Indolyl | H | H | R, S | 0 | Phenyl | MeOH | C24H19N3O4 | 265-266 | 0.34** |
| 34 | 2-Indolyl | H | H | R, S | 0 | Methyl | MeOH | C19H17N3O4 | 274-276 | 0.34* |
| 35 | 1-Methyl-2-indolyl | H | H | R, S | 0 | Ethyl | MeOH | C21H21N3O4 | 220-221 | 0.40* |
| 36 | 1-Methyl-2-indolyl | H | H | R, S | 0 | Propyl | MeOH | C22H23N3O4 | 223-224 | 0.65* |

TABLE 1-continued

COMPOUNDS OF GENERAL FORMULA (I)

(I)

| COMPOUND | R1 | R2 | R3 | STEREO (Note 1) | n | R4 | SOLVENT OF CRYATALLISATION | FORMULA | FUSION POINT (C) ° | TLC (Rf) (Note 2) |
|---|---|---|---|---|---|---|---|---|---|---|
| 37 | 1-Methyl-2-indolyl | H | H | R, S | 0 | Butyl | MeOH | C23H25N3O4 | 192-193 | 0.70* |
| 38 | 2-Indolyl | H | H | R, S | 0 | Pentyl | EtOH 96% | C23H25N3O4 | 241-243 | 0.76* |
| 39 | 2-Indolyl | H | H | R, S | 0 | Hexyl | EtOH 96% | C24H27N3O4 | 258-260 | 0.56* |
| 40 | 2-Indolyl | H | H | R. S | 0 | Heptyl | MeOH | C25H29N3O4 | 242-243 | 0.64* |
| 41 | 2-Indolyl | H | H | R, S | 0 | Isopropyl | EtOH 99% | C21H21N3O4 | 276-277 | 0.58* |
| 42 | 2-Indolyl | H | H | R, S | 1 | Isopropyl | MeOH | C22H23N3O4 | 257-259 | 0.51** |
| 43 | 2-Indolyl | H | H | R, S | 2 | Isopropyl | AcOEt | $C_{23}H_{25}N_3O_4$ | 252-253 | 0.73* |
| 44 | 2-Indolyl | H | H | R, S | 3 | Isopropyl | AcOEt | $C_{24}H_{27}N_3O_4$ | 247-248 | 0.83* |
| 45 | 2-Indolyl | H | H | R, S | 4 | Isopropyl | AcOEt | $C_{25}H_{29}N_3O_4$ | 240 dec | 0.78* |
| 46 | 2-Indolyl | H | H | R, S | 0 | 2-Ethyl-butyl | MeOH | $C_{24}H_{27}N_3O_4$ | 218-219 | 0.68* |
| 47 | 2-Indolyl | H | H | R, S | 1 | 2-Ethyl-butyl | EtOH 99% | $C_{25}H_{29}N_3O_4$ | 217-218 | 0.77* |
| 48 | 2-Indolyl | H | H | R, S | 1 | Cyclohexyl | MeOH | $C_{25}H_{27}N_3O_4$ | 222-223 | 0.58* |
| 49 | 2-Indolyl | H | H | R, S | 2 | Cyclohexyl | EtOH 95% | $C_{26}H_{29}N_3O_4$ | 268-269 | 0.63* |
| 50 | 2-Indolyl | H | H | R, S | 3 | Cyclohexyl | AcOEt | $C_{27}H_{31}N_3O_4$ | 241-242 | 0.86* |
| 51 | 2-Indolyl | H | H | R, S | 2 | Methylsulfanyl | MeOH | $C_{21}H_{21}N_3O_4S$ | 250-251 | 0.38* |
| 52 | 2-Indolyl | H | H | R, S | 1 | Phenylsulfanyl | MeOH | $C_{25}H_{21}N_3O_4S$ | 252-253 | 0.56* |
| 53 | 2-Indolyl | H | H | R, S | 1 | 1-Adamantylsulfanyl | EtOH 95% | $C_{29}H_{31}N_3O_4S$ | 261-263 | 0.49* |
| 54 | 2-Indolyl | Methyl | H | R, S | 1 | Phenyl | AcOEt | $C_{26}H_{23}N_3O_4S$ | 191-193 | 0.26* |
| 55 | 3-Indolyl | H | H | R, S | 1 | Phenyl | MeOH | $C_{25}H_{21}N_3O_4$ | 223-224 | 0.40* |

($^a$) Enantiomer R $[\alpha]^{25}_D$ = +35.4° (C = 0.65; DMF); ($^b$) Enantiomer S $[\alpha]^{25}_D$ = −34.8° (C = 0.65; DMF)
Note 1
Configuration of the carbon labeled (*) in the general formula (I);
Note 2
*Eluent, AcOEt/MeOH 2:1 (v/v); **Eluent, AcOEt/MeOH 3:1 (v/v).

DESCRIPTION OF THE PHARMACOLOGICAL ACTIVITY

1. Anti Cholecystokinin Activity (Anti CCK-1) In Vitro.

To evaluate the capacity of the compounds forming the subject of the invention to interact with the CCK-1 receptors, binding tests were performed on isolated rat pancreatic acini, using as marked binder the [$^{125}$I]-BH-CCK-8 solphate, according to the procedure described by Makovec F. [J. Med. Chem. 35, (1992), 28]. The pancreatic acini obtained from the outbred male rat pancreas of the Sprague Dawley strain, were incubated in the presence of radioactive tracers and the compound studied for 30 minutes at 37° C. After having discarded the supernatant, the radioactivity associated with the pellet was determined with a liquid scintillator. The specific binding was determined as the difference between the binding in the absence and in the presence of CCK-8, $1.10^{-6}$M. The results obtained are shown in Table 2, in which IC$_{50}$ is reported, that is to say the concentration (expressed in micromoles/litre) of the antagonist capable of displacing by 50% the [$^{125}$I]-BH-CCK-8 from the receptor. The values of IC$_{50}$ reported were calculated with the progression method of a set of at least 3 experiences for each compound studied.

From the data plotted in Table 2 it can be seen that many of the compounds forming the subject of the invention, such as for example compounds 21, 23, 25, 26, 30 and 32 are potent inhibitors of the binding of [$^{125}$I]-BH-CCK-8 to the CCK-1 receptors of the pancreatic acini of rat, exhibiting an infinity at nanomolar level.

2. Anti Cholesystokinin Activity (Anti CCK-2) In Vitro

Whereby to verify the hypothesis that the compound forming the subject of the invention would be specific CCK-1 antagonist, it was tested for some of the more active compounds, what CCK-1 antagonists also exhibited possible infinity for the central receptors of the CCK of CCK-2 type. For this purpose binding tests were performed on cerebral cortex of male albino guinea pigs outbred from the Hartley strain, using as marked binder the [$^{125}$I]-BH-CCK-8 sulphate, according to the procedure described by Makovec F. [J. Med. Chem. 35, (1992),28].

TABLE 2

Inhibition of binding of [$^{125}$I] -BH-CCK-8 to isolated rat pancreatic acini

| Compound IC$_{50}$ | (micromoles/liters) |
|---|---|
| 1 | 0.24 |
| 2 | 0.11 |
| 3 | 7.13 |
| 4 | 0.41 |
| 5 | 0.17 |

TABLE 2-continued

Inhibition of binding of [$^{125}$I]-BH-CCK-8 to isolated rat pancreatic acini

| Compound | IC$_{50}$ (micromoles/liters) |
|---|---|
| 6 | 0.06 |
| 7 | 0.16 |
| 8 | 0.09 |
| 9 | 0.52 |
| 10 | 0.78 |
| 11 | 0.16 |
| 12 | 0.37 |
| 13 | 0.27 |
| 14 | 0.28 |
| 15 | 1.41 |
| 16 | 0.24 |
| 17 | 0.16 |
| 18 | 0.43 |
| 19 | 0.18 |
| 20 | 0.014 |
| 21 | 0.009 |
| 22 | 0.19 |
| 23 | 0.007 |
| 24 | 0.09 |
| 25 | 0.007 |
| 26 | 0.009 |
| 27 | 0.03 |
| 28 | 0.12 |
| 29 | 0.12 |
| 30 | 0.008 |
| 31 | 0.01 |
| 32 | 0.009 |
| 33 | 0.26 |
| 34 | 1.96 |
| 35 | 3.08 |
| 36 | 0.21 |
| 37 | 0.17 |
| 38 | 0.01 |
| 39 | 0.02 |
| 40 | 0.24 |
| 41 | 0.20 |
| 42 | 0.06 |
| 43 | 0.08 |
| 44 | 0.04 |
| 45 | 0.14 |
| 46 | 0.03 |
| 47 | 0.02 |
| 48 | 0.02 |
| 49 | 0.04 |
| 50 | 0.17 |
| 51 | 0.04 |
| 52 | 0.62 |
| 53 | 0.03 |
| 54 | 0.11 |
| 55 | 1.95 |

The incubation of the cerebral membranes together with the radioactive tracers and the compounds under study was effected on multi-well plates for 120 minutes at 25° C. Each well contained membrane corresponding to about 0.5 mg of proteins/ml and 25 pM of marked binder in a total volume of 250 micro litres. The specific binding was determined as the difference between the binding in the absence and in the presence of CCK-8, $1.10^{-6}$M. At the end of the incubation a rapid filtration of the plate was performed under vacuum and the radioactivity of the individual filters extracted from the wells was measured with a γ-emission counter. The results obtained are shown in Table 3, in which the tested compounds are indicated, the IC$_{50}$ calculated with the regression method on a set of at least 3 tests for each compound studied and an index derived from the ratio of the affinity obtained for the two types of receptor CCK-2 and CCK-1.

TABLE 3

Inhibition of the binding of [$^{125}$I]-BH-CCK-8 to the cortical membrane of guinea pigs:

| Compound | IC$_{50}$ (micromoles/liter) | Ratio $\frac{IC_{50}CCK-2}{IC_{50}CCK-1(*)}$ |
|---|---|---|
| 6 | 10.6 | 176.6 |
| 20 | 2.22 | 158.6 |
| 21 | 3.8 | 422.2 |
| 23 | 10.8 | 1542.9 |
| 25 | >30 | >4286 |
| 26 | 5.15 | 572.2 |
| 30 | 3.5 | 437.5 |
| 31 | 3.4 | 340 |
| 32 | 5.68 | 631.1 |
| 38 | >30 | >3000 |
| 39 | >30 | >1500 |
| 41 | 27.4 | 137 |
| 46 | 2.67 | 89 |
| 47 | 14.8 | 740 |
| 48 | 1.22 | 61 |

Note
(*): Data drawn from Table 2

From the results shown in Table 3 it emerges that the compounds in question bind the central receptor CCK-2 weakly, their affinity being on average for this receptor from 100 to 1000 times less than that shown for the receptors of CCK-1 type. By comparing these values of affinity with those obtained for the CCK-1 receptors previously indicated in Table 2 it can be affirmed that the compounds in question are potent binders specific for receptor CCK-1.

To verify the hypothesis that the subject compounds would be CCK-1 specific antagonists and not agonists, several tests were made of the more active compounds illustrated in Table 2 of the CCK-1 antagonist activity on a functional model. A guinea pig gall bladder stimulated in vitro by CCK-8 according to the method described by Makovec et al. was used as an experimental model. [Arzneim. Forsch. Drug Res. 35 (7), 1048 (1985)]. The results thus obtained are illustrated in the following Table 4 in which the values of IC$_{50}$ (moles/litre) are reported.

The IC$_{50}$ reported in Table 4 represent for each compound the average of at least two separate experiments, each with 6-8 concentrations.

TABLE 4

Inhibition of the in vitro induced contraction of guinea pig gall bladder by CCK-8 (5 ng/ml)

| Compound | IC$_{50}$ (moles/liter) |
|---|---|
| 20 | $3.5 \times 10^{-8}$ |
| 21 | $2.0 \times 10^{-8}$ |
| 23 | $1.5 \times 10^{-8}$ |
| 25 | $0.8 \times 10^{-8}$ |
| 26 | $4.3 \times 10^{-8}$ |
| 30 | $3.0 \times 10^{-8}$ |

From the data reported in the Table it is shown how some of the compounds forming the subject of the invention are provided with a potent antagonist activity against CCK even in a functional model.

Moreover, none of the products tested presented appreciable agonist properties up to the maximum tested concentration ($1 \times 10^{-5}$M).

The invention claimed is:

1. Compounds which can be represented by the below indicated general formula (I) and in which:

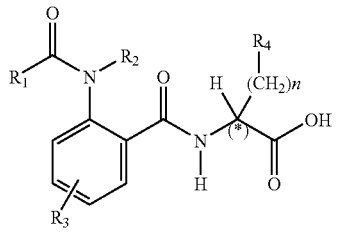

n is a whole number lying between 0 and 7;
$R_1$ is chosen independently from the groups:

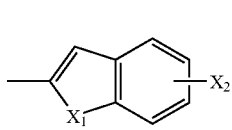 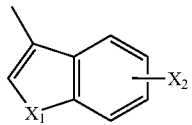

in which $X_1$ is chosen independently from S, O, $NR_2$ and $X_2$ is a group chosen independently from: H, $C_1$-$C_4$ linear or branched alkile, F, Cl, $CF_3$, $OCH_3$, $OC_2H_5$, CN;

$R_2$ is chosen independently from H or $CH_3$;
$R_3$ is chosen independently from H, $CH_3$, F, Cl, $CF_3$, $OCH_3$;
$R_4$ is chosen independently from the groups: H, —S—$(CH_2)m$-$R_5$, -$SO_2$—$(CH_2)m$-$R_5$ (n different from 0) in which m is a whole number lying between 0 and 2, a branched alkyl group formed by 3-6 carbon atoms, a cyclo alkyl formed by 3-10 carbon atoms, a cyclo alkanyl formed by 4-6 carbon atoms, the group 1 or 2-adamantile, a simple or mono- or bi-substituted phenyl group, in which the substituents can be chosen independently from halogens, a linear alkyl group formed by 1-3 carbon atoms, a branched alkyl group formed by 3-6 carbon atoms, an alkoxylic group formed by 1-3 carbon atoms, —$NO_2$, —$CF_3$, —CN;
$R_5$ is chosen from the groups: H, a linear alkyl group formed by 1-3 carbon atoms, a branched alkyl group formed by 3-6 carbon atoms, a cyclo alkyl formed by 3 up to 10 carbon atoms, the group 1 or 2 adamantile, a simple or mono- or bi-substituted phenyl group in which the substituents can be chosen independently from halogens, a linear alkyl group from 1 to 3 carbon atoms, a branched alkyl group formed by 3-6 carbon atoms, an alkoxylic group formed by 1-3 carbon atoms, —$NO_2$, —$CF_3$, —CN, and their pharmaceutically acceptable salts; the stereo chemical chiral centre, indicated with an asterisk (*) in formula (I) can be R (Rectus), racemic [R (Rectus), S (Sinister)]or S (Sinister).

2. Compounds according to claim 1 of general formula (I), simple or as salts, in which $R_1$ is the group 2-indolyl simple or independently substituted in position 1 with the methyl group or in position 5 with the flouro group.

3. Compound according to claim 1, in which $R_2$ and $R_3$ are H.

4. Compound according to claim 1, in which n is 1 or 2 and $R_4$ is the simple phenyl group or phenyl group substituted with the methyl, flouro or methoxy groups.

5. Compound according to claim 1, in which the stereochemistry of the chiral centre marked with an asterisk (*) in (I) is R (Rectus) or RS (raceme).

6. Compounds according to claim 1 of general formula (I), simple or as salts, in which $R_1$ is the group 2-indolyl, either simple or independently substituted in position 1 with the methyl group or in position 5 with the flouro group, $R_2$ and $R_3$ are H, n is 1 or 2, $R_4$ is the simple phenyl group or the phenyl group substituted with the methyl, flouro or methoxy groups and the stereochemistry of the chiral centre marked with an asterisk (*) in (I) is R (Rectus), or RS (raceme).

7. Pharmaceutical preparation including as active substance at least one of the compounds according to any of claim 1 or a pharmaceutical acceptable salt thereof.

8. Process for the preparation of a derivative of the general formula (I) in which $R_1$, $R_2$, $R_3$ and $R_4$ and n are as defined in claim 1 and in which the substitutents on the chiral centre marked with an asterisk (*) have the configuration R, S or (R,S) (raceme), which comprise the operations of:

a) Reacting in stiochiometric ratio the hydrochloride of the ethyl ester of the amino acids of formula (V) in which n and $R_4$ have the above indicated definition and have the chiral centre in the desired configuration, with the isatoic anhydride of formula (TV) suitably substituted with $R_2$ and $R_3$ in which $R_2$ and $R_3$ have the above indicated definition, in the presence of a tertiary amine such as, for example, triethylamine, in an inert solvent and at a temperature lying

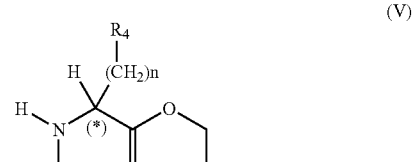

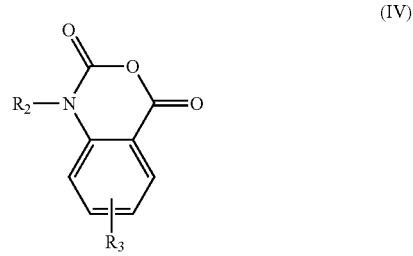

between +10° C. and the boiling temperature of the solvent, to give the N-anthranoyl -amino acid ethyl esters of formula (ITT)

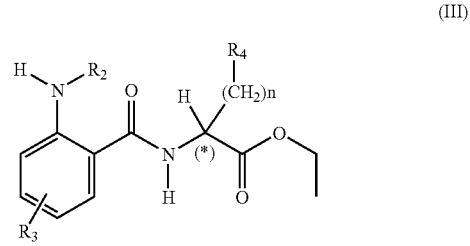

b) Reacting the anthranilic derivatives of formula (ITT), in which n, $R_2$, $R_3$ and $R_4$ have the above indicated definition, with an equivalent quantity of an acyl chloride of formula $R_1$-COCl, in which $R_1$ has the above indicated definition, preferably in pyridine and at a temperature lying between 0° C. and +30° C. and recovering from the reaction mixture the acyl derivatives of formula (TI).

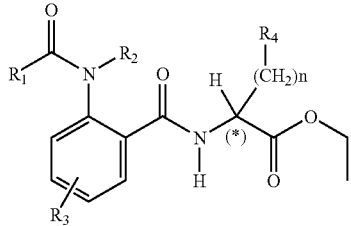

(II)

c) Hydrolising the esters of formula (TI), in which n, $R_1$, $R_2$, $R_3$, and $R_4$ have the above indicated definition, in an inert solvent (such as tetrahydrofuran for example) with an aqueous solution of a strong inorganic base (such as lithium hydroxide) for a period of time lying between 4 and 48 hours. After evaporation of the solvent and acidification, recovering from the reaction mass the derivatives of the anthranylic acid of formula (I).

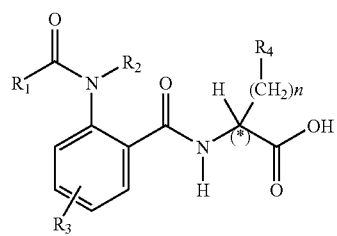

(I)

in which n $R_1$, $R_2$, $R_3$ and $R_4$ have the above indicated definition and with the chiral centre in the desired configuration. The final compounds of formula (I) are isolated as such or as pharmaceutically acceptable salts and purified by conventional methods.

* * * * *